(12) United States Patent
Sakurai

(10) Patent No.: US 6,242,753 B1
(45) Date of Patent: Jun. 5, 2001

(54) PORTABLE STERILIZING APPARATUS

(75) Inventor: Yoshihiro Sakurai, Tokyo (JP)

(73) Assignee: Kabushiki Kaisha Lucent, Tokyo (JP)

( * ) Notice: Subject to any disclaimer, the term of this patent is extended or adjusted under 35 U.S.C. 154(b) by 0 days.

(21) Appl. No.: 09/212,963

(22) Filed: Dec. 16, 1998

(30) Foreign Application Priority Data

Dec. 25, 1997 (JP) .................................................. 9-366287

(51) Int. Cl.⁷ .................................................. A61L 2/10
(52) U.S. Cl. ................................ 250/504 R; 250/504 H; 250/493.1; 250/455.11
(58) Field of Search ........................... 250/504 R, 504 H, 250/493.1, 455.11

(56) References Cited

U.S. PATENT DOCUMENTS

| | | | | |
|---|---|---|---|---|
| 4,896,042 | * | 1/1990 | Humphreys | 250/435 |
| 5,029,252 | * | 7/1991 | Ameseder | 250/455.1 |
| 5,920,075 | * | 7/1999 | Whitehead | 250/492.1 |
| 6,005,254 | * | 12/1999 | Wijtsma et al. | 250/494.1 |

FOREIGN PATENT DOCUMENTS

| | | |
|---|---|---|
| 6-154300 | 6/1994 | (JP) . |
| 3012680 | 4/1995 | (JP) . |

* cited by examiner

*Primary Examiner*—Jack Berman
*Assistant Examiner*—Nikita Wells
(74) *Attorney, Agent, or Firm*—Jordan and Hamburg LLP

(57) ABSTRACT

A portable sterilizing apparatus has a main housing having a bottom surface, a flange portion formed to extend parallel with the bottom surface, a replaceable sterilizing lamp an irradiating unit having a shade member for supporting the sterilizing lamp pivotally on a top portion of the housing allowing rotation upward from a front surface of the housing. The main housing is provided with a power source and a controller for controlling the conduction of electric power from the power source. The controller comprises an automatic switch, for turning OFF electric power supplied to the irradiating unit when the irradiating unit assumes a closed position, a timer for limiting the operation time of the sterilizing lamp in an open position, a manual switch for turning ON the sterilizing lamp after the passage of the time limited by the timer, and a lamp indicating that the sterilizing lamp is ON.

20 Claims, 4 Drawing Sheets

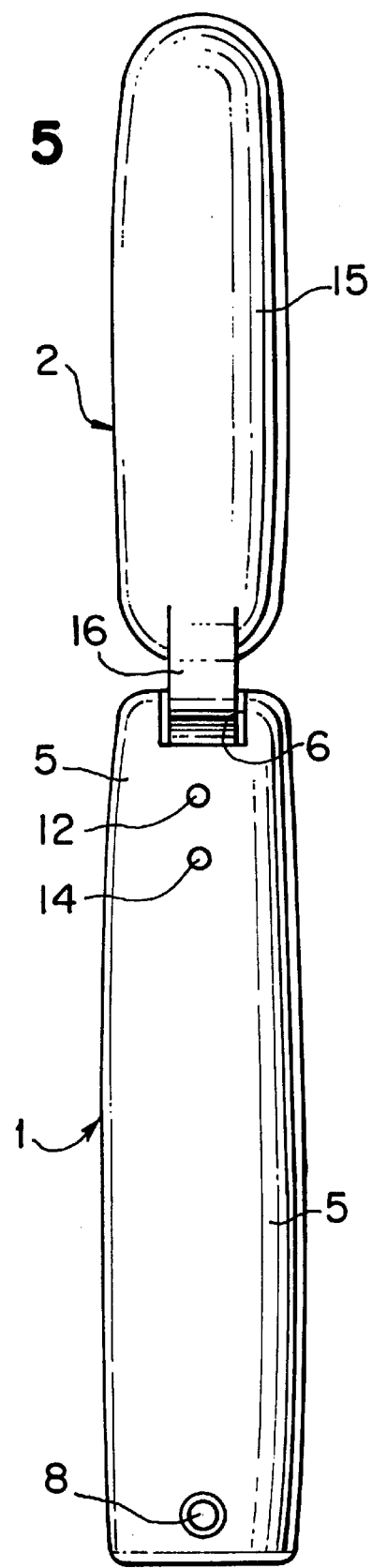
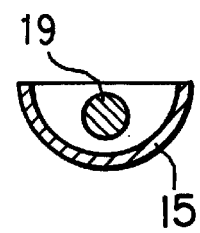

PORTABLE STERILIZING APPARATUS

BACKGROUND

The present invention relates to a portable sterilizing apparatus for sterilizing and disinfecting instruments used in medical treatment, beauty care, and the like.

In the past, sterilization and disinfection have been accomplished by moving the article to be sterilized to a sterilizing apparatus in the form of a large and immovable box, and the article to be sterilized was sterilized while being housed in a sterilizing chamber of the apparatus.

In view of the foregoing, a sterilizing apparatus has been proposed which can be moved on casters, as disclosed in Japanese Patent Application Laid-Open Publication NO. 6-154300. A holder is provided on a doctor table and holds articles to be sterilized with a sterilizing lamp. A sterilizing lamp irradiates the article, such as a medical implement, mounted on the holder. In the sterilizing apparatus as described, it is necessary to change a size of a housing portion of the article to adjust to the size of the article. Thus, the apparatus becomes very large depending on the size of the article to be sterilized.

Further, a stand type sterilizing apparatus as disclosed in Japanese registered Utility Model Publication No. 3012680 has been proposed. A sterilizing lamp is moved to locations such as a hotel, a restaurant or the like, where an entire room requires sterilization. However, this type of sterilizing apparatus may be damaged while being moved by accidentally being bumped into walls and other objects. Further, while this apparatus includes a motion sensor, as a safety mechanism in case a person walks into the area, it is not effective in high traffic areas.

SUMMARY OF THE INVENTION

It is an object of the present invention to provide a portable sterilizing apparatus capable of being brought to the instruments, rather than the instruments being brought to the sterilizing apparatus. It is a also object of the present invention that it be capable of being carried by a single person.

It is a further object of the present invention to reduce the likelihood of accidentally damaging the sterilization apparatus while it is being moved.

It is yet another object of the present invention to provide a portable sterilizing apparatus that may be safely utilized in high traffic areas, such as barber shops and stores, without harming people.

BRIEF DESCRIPTION OF THE DRAWINGS

FIG. 5 is a back view of the portable sterilizing apparatus, in an open turned on position, according to the present invention; and FIG. 6 is a sectional view, taken along line VI—VI of FIG. 3, of an irradiation unit of the portable sterilizing apparatus according to the present invention.

DETAILED DESCRIPTION

Figure 1:
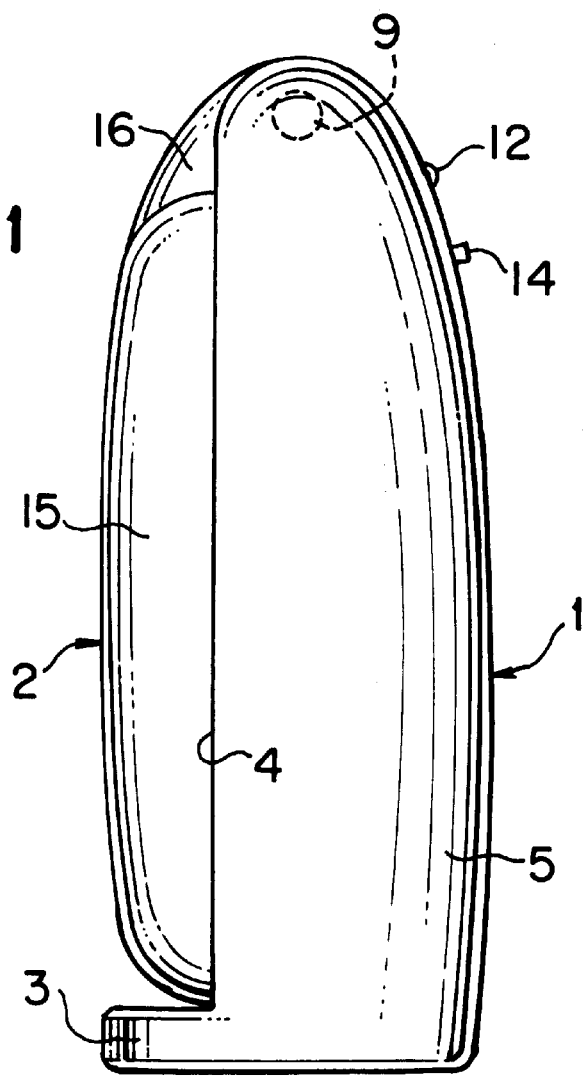
FIG. 1 is a side view of a portable sterilizing apparatus, in a closed shut off position, according to the present invention.

A portable sterilizing apparatus according to the present invention is explained hereinafter with reference to the drawings. Referring to FIG. 1, the portable sterilizing apparatus according to the present invention comprises a main housing 1, and an irradiating unit 2 mounted on the housing 1, rotatable upwards from a position in contact with the housing 1.

Figure 2:
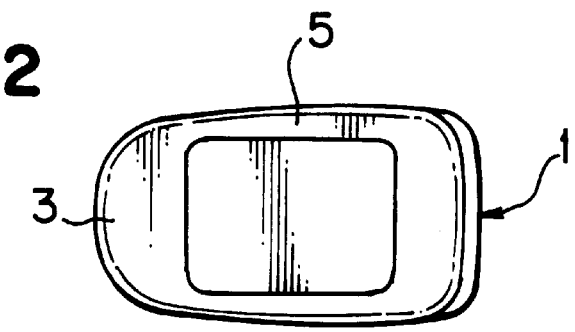
FIG. 2 is a bottom view of the portable sterilizing apparatus, in a closed shut off position, according to the present invention.

The main housing 1 of the portable sterilizing apparatus comprises, as shown in FIGS. 1 and 2, a bottom surface horizontal to a floor surface, a top generally in the form of a circular arc, a front surface 4 extending vertically toward the bottom, and a rear surface extending generally vertically from the bottom surface opposite to the front surface 4. A swelled intermediate portion, to provide for easy carrying, which is curved generally from the intermediate portion toward the top A box 5 has converging sides, generally in the form of a circular arc with a longitudinal width that is wider than a lateral width, and has a flange portion 3 shaped in the form of a laterally inverted C at the lower part of the front surface 4 and extending parallel with the bottom surface.

Figure 3:
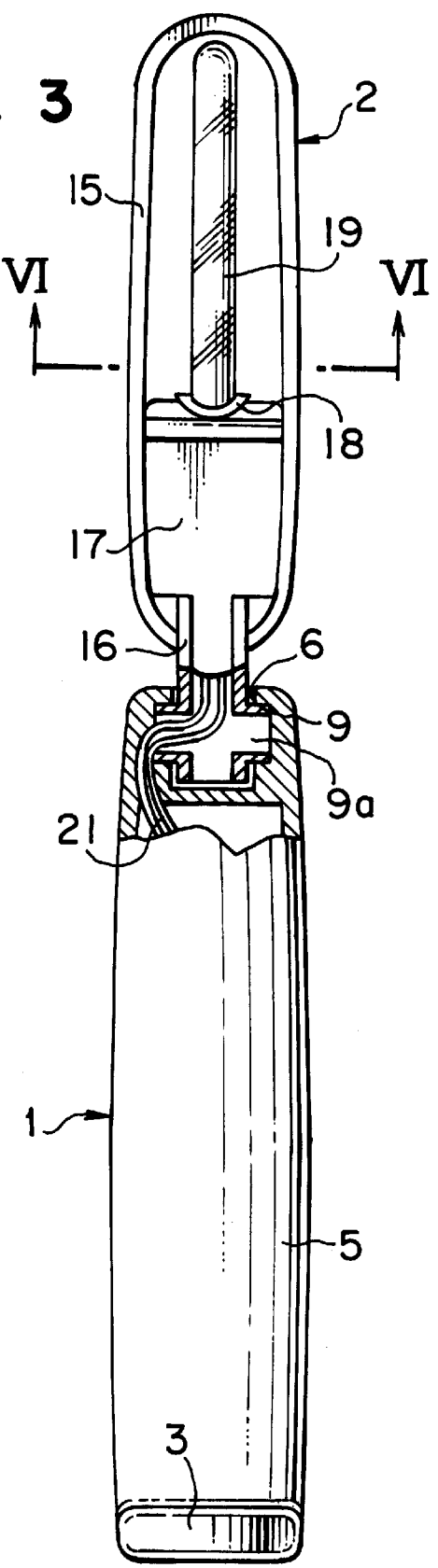
FIG. 3 is a front view, partially in cross section, of the portable sterilizing apparatus, in an open turned on position, according to the present invention.

As shown in FIGS. 3 and 5, the main housing 1 of the portable sterilizing apparatus is provided at the upper end with a mounting groove 6 opened longitudinally and upward at a central position of the lateral width.

The main housing 1 is preferably sized to be portable, such that the height is approximately 130 mm, the longitudinal width of the bottom surface is approximately 40 mm, and the lateral width is approximately 28 mm.

Figure 4:
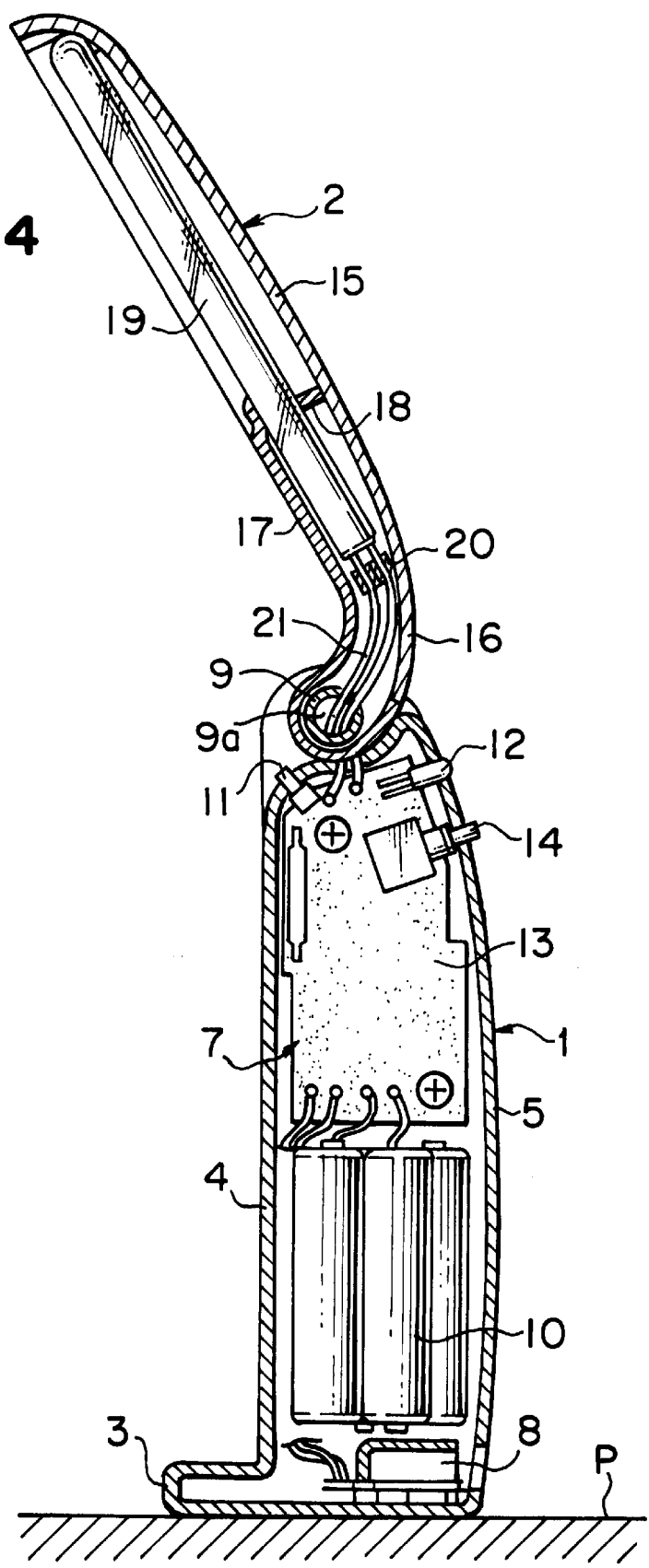
FIG. 4 is a vertical cross sectional side view of the portable sterilizing apparatus, in an open turned on position, according to the present invention.

As shown in FIG. 4, the main housing 1 has a bracket 8 for connection to an external power source and a power source portion 10 such as a storage battery charged by the external power source, and a controller 7 for controlling electric conduction. Controller 7 includes an automatic switch 11 for turning OFF the power supplied to the irradiating unit 2, when the sterilization apparatus is in a closed shut off position. A timer circuit 13 the time power is supplied to the irradiating unit 2, and a manual switch 14 allows for restarting the timer circuit 13. It is noted that the power source portion 10 can be replaced by a dry battery instead of the storage battery.

The irradiating unit 2 has a shade member 15, which is long in a longitudinal direction of the apparatus and has a longitudinal end portion shaped in the form of a semicircular arc as shown in FIG. 3 and 6. A mounting arm 16 has a curved shape and is formed integrally generally at a rear central position of the shade member 15, with a shaft portion 9 projecting on both sides and housed within the mounting groove 6.

Further, as shown in FIGS. 3 and 4, the sterilizing unit 2 is provided with a detachably mounted lamp holder 17 for supporting a replaceable sterilizing lamp 19.

Sterilizing lamp 19 is a small low-voltage mercury lamp of a cold cathode type covered by ordinarily manufactured quartz glass, and at peak times emits a wavelength of 185 nm and 254 nm with a power output of 3 W to 5 W. The sterilizing lamp 19 is approximately 64 to 66 mm in the length and 6.0 to 6.6 mm in diameter.

In addition, the irradiating unit 2 has, as shown in FIGS. 3 and 6, a holding portion 18 for holding a rear portion of the sterilizing lamp 19 on an inner surface and in contact with a front end of the lamp holder 17. An electric socket 20 (FIG. 4) is connected to a terminal electrode of the sterilizing lamp 19, held on the holding portion 18, on the inner surface at the rear of the lamp holder 17. The electric socket 20 is connected to a lead wire 21, inserted into a center hole 9a bored in the center of the shaft portion 9 of the mounting arm 16, and the lead wire is connected to the timer circuit 13.

The mounting arm 16 is fitted in the mounting groove 6, provided in the top portion of the main housing 1, and is pivotally supported on the top portion of the main housing 1 around the shaft portion 9.

The irradiating unit 2 is folded, with the shade member 15 in contact with the front surface 4 of the main housing 1, when the portable sterilizing apparatus is in a closed shut off position. The longitudinal length of the irradiating unit 2 is such that, when folded in the main housing 1, the front end of the irradiating unit 2 comes into contact with the flange portion 3 of the main housing 1 and the shade member 15 comes in contact with the front surface 4 of the main housing 1. The interior of the shade member 15 houses sterilizing lamp 19 and the side of the shade member 15 is settled in the longitudinal width of the flange portion 3.

Accordingly, when the portable sterilizing apparatus according to the present invention is not being used, the irradiating unit 2 is folded, and the upper surface of the shade member 15 contacts the vertical surface of the main housing 1, and can be held and carried.

Where the portable sterilizing apparatus according to the present invention is being used, the apparatus is made to stand upright on a surface P of a table, and the irradiating unit 2 is turned upward from the main 1 and adjusted to a position opposite to an article to be sterilized. At that time, the irradiating unit 2 can be rotated fractionally with respect to the main 1 and held in position at a suitable angle. The range at which the irradiating unit can be rotated is approximately from 0 to about 150 degrees.

When the irradiating unit 2 is rotated upward, the automatic switch 11 of controller 7 is automatically closed to turn the sterilizing lamp 19 on. When the sterilizing lamp 19 is turned on, a lighting display lamp 12 is also turned on.

Accordingly, a user engaged in disinfection and sterilization is alerted to avoid looking straight at the front surface of the irradiating unit 2.

The timer circuit 13 is generally set for 30 seconds of operation. That is, when the time of the timer circuit 13 has passed 30 seconds, the sterilizing lamp 19 is put out by being controlled by the timer circuit 13.

Further, when the irradiating unit 2 is rotated downward and folded as described above, even before the 30 second period has elapsed, the automatic switch 11 is opened so that the sterilizing lamp 19 is turned OFF, and operation is discontinued.

The operating time of the sterilizing lamp 19 is set in accordance with the results of testing the sterilizing effect by ZAIDANHOJIN (Foundational Juridical Person) Japanese Food Analyzing Center. Test germs used in the test are NB culture medium of EIKEN CHEMICAL K.K.: ordinary Bouillon culture medium and SA culture medium: *Escherichia coli* IFO 3301 (coliform bacilli) cultured by standard agar. This test germ was prepared by being inoculated in the NB culture medium, being cultured for 20 hours at 85° C., and having the obtained culture liquid diluted by sterilized water so as to have the germ number of approximately 105/ml to provide a germ liquid.

In the testing operation, 300 ml of germ liquid was placed into a 300 ml glass beaker (diameter: approximately 75 mm). A lamp portion of the sterilizing lamp, as an examining portion, was inserted into the center portion of the glass beaker, and the sterilizing lamp was operated for 10, 20 and 30 seconds. In the measuring process, the number of raw germs in the germ liquid before irradiation and the number of raw germs in the germ liquid after irradiation for 10, 20 and 30 seconds were measured by a mixing flat-plate culturing process (culturing for two days at 35° C.) using the SA culture medium.

As is apparent from the test results shown in Table 1, the germ liquid subjected to irradiation for 30 seconds, the number of raw germs was reduced most effectively.

TABLE 1

| Irradiation time | Number of raw germs per 1 ml |
|---|---|
| 0 (before irradiation) | $7.9 \times 10^6$ |
| 10 seconds | $1.5 \times 10^5$ |
| 20 seconds | $1.2 \times 10^4$ |
| 30 seconds | $3.3 \times 10^2$ |

Incidentally, in the portable sterilizing apparatus according to the present invention, where the time of 30 seconds preset by the timer circuit 13 has passed, the sterilizing lamp 19 can be turned on again by depressing the manual switch 14 provided on the main housing 1.

Further, in the main housing 1 of the portable sterilizing apparatus according to the present invention, since the rear surface thereof has a swell so as to be carried easily and the sterilizing lamp 19 is mounted in the irradiating unit 2 as previously mentioned, where the irradiating surface of an article to be sterilized is wide, a user may rotate the irradiating unit 2 upward to oppose the sterilizing lamp 19 to the article to be sterilized, move the main housing 1 by hand in a lateral direction along the surface of the article, and sterilize and disinfect the article by the repetition of the opening and closing operation of the irradiating unit 2 or operation of the manual switch 14.

Further, in the portable sterilizing apparatus according to the present invention, the irradiating unit 2 is folded to the front surface 4 of the main 1 whereby the inner surface of the shade member 7 is closed by the inner surface 4 of the main housing 1, thereby protecting the sterilizing lamp 19 during transport from the shock caused by contact with foreign objects.

The portable sterilizing apparatus according to the present invention permits its lighting state to be known by the lighting display lamp 12, so it is possible to alert the user so the user does not erroneously look straight at the sterilizing lamp 19.

Further, since the lighting time of the sterilizing lamp 19 is preset by the timer circuit 13, even if the user is engaging in other work at a distant place, he can sterilize and disinfect the article safely.

In addition, the sterilizing lamp 19 can be extended depending on the condition of the article to be sterilized, but since the time to be extended is limited to a present time, it is possible to avoid mistakes by the user such as not setting a termination time.

What is claimed is:

1. A portable sterilizing apparatus for sterilizing an object, comprising:

a main housing having an outer surface including, a top, a front side, lateral sides, and a back side;

an irradiating unit including a lampshade member and an ultra violet lamp housed in said lampshade member, said lampshade member defining a lampshade opening via which said ultra violet lamp emits ultra violet radiation onto said object;

a pivot mount for pivotally mounting said irradiating unit to said top of said main housing such that said lampshade member is pivotable from a closed position, whereat said lampshade opening is closed by said front side of said main housing, to an open position whereat said lampshade member is supported with said lampshade opening displaced from said front side of said main housing so as to permit ultra violet radiation from said ultra violet lamp to exit and irradiate said object; and an electric source controller disposed in said main housing and electrically connected to said ultra violet lamp to effect operation of said ultra violet lamp.

2. The portable sterilizing apparatus of claim 1 further comprising a power source housed in said main housing and connected to said electric source controller for powering said ultra violet lamp.

3. The portable sterilizing apparatus of claim 1 wherein said back side of said main housing has a convex shape curved toward the top.

4. The portable sterilizing apparatus of claim 1 wherein:

said pivot mount includes said lampshade member having an end portion and an arm extending therefrom, said arm having opposing sides and a shaft laterally extending from each of said opposing sides; and said top of said main housing having a recess with sides each defining a hole for accepting said shafts extending from said opposing sides of said arm so as to support said lampshade member at said open position.

5. The portable sterilizing apparatus of claim 4 wherein said irradiating unit has a lamp holder member detachably installed in said end portion of said lampshade member for holding said ultra violet lamp in position in conjunction with said lampshade member, said lamp holder member covering a connection end of said ultra violet lamp to shield electrical connection thereto and being detachable to permit replacement of said ultra violet lamp.

6. The portable sterilizing apparatus of claim 1 wherein said irradiating unit has a lamp holder member detachably installed in said end portion of said lampshade member for holding said ultra violet lamp in position in conjunction with said lampshade member, said lamp holder member covering a connection end of said ultra violet lamp to shield electrical connection thereto and being detachable to permit replacement of said ultra violet lamp.

7. The sterilizing apparatus claimed in claim 1 wherein said main housing has a depth length between the front side and the back side greater than a lateral length between said lateral sides, and a flange outwardly extending at a lower front portion of said main housing to permit said apparatus to be stood upright with said lampshade member at said open position.

8. The sterilizing apparatus claimed in claim 7 wherein said main housing has a height of about 130 mm, and a bottom including said flange has a depth of about 40 mm, and the lateral length is about 28 mm.

9. The sterilizing apparatus claimed in claim 1 wherein said electric source controller includes an automatic switch for turning off said ultra violet lamp in response to said irradiating unit being moved to said closed position.

10. The sterilizing apparatus claimed in claim 1 wherein said electric source controller includes an indicator lamp to indicate said ultra violet lamp is turned on.

11. The sterilizing apparatus claimed in claim 1 wherein said electric source controller includes a timer circuit for limiting operation of said ultra violet lamp to a set time period, and a mannual switch for restarting operation of the timer circuit.

12. The sterilizing apparatus claimed in claim 11 wherein said set time period is 30 sec.

13. The sterilizing apparatus claimed in claim 1 wherein said ultra violet lamp has a power output of 3 W to 5 W and provides ultra violet emission at a wavelength of at least one of 185 and 254 nm.

14. The sterilizing apparatus claimed in claim 1 wherein said irradiating unit pivots from said closed position to said open position through an angle of about 0 to about 150 degrees.

15. A portable sterilizing apparatus for sterilizing an object, comprising:

a main housing having an outer surface including, a top, a front side, lateral sides, and a back side, said main housing being vertically elongated;

an irradiating unit having a radiating aperture through which light is radiated;

a coupling structure for movably mounting said irradiating unit to said main housing such that said irradiating unit is movable from a closed position, whereat said radiating aperture is closed by said front side of said main housing, to an open position whereat said irradiating unit is supported with said radiating aperture displaced from said front side of said main housing so as to permit light to exit and irradiate said object when said object is disposed under said irradiating unit; and an electrical circuit for distributing electric power to said irradiating unit.

16. The portable sterilizing apparatus of claim 15 further comprising a power source housed in said main housing and connected to said electric circuit for powering said irradiating unit.

17. The sterilizing apparatus claimed in claim 15 wherein said main housing has a flange outwardly extending at a lower front portion of said main housing to permit said sterilizing apparatus to be stood upright with said irradiating unit at said open position.

18. The sterilizing apparatus claimed in claim 17 wherein said electric circuit includes an automatic switch for turning off said irradiating unit in response to said irradiating unit being moved to said closed position.

19. The sterilizing apparatus claimed in claim 15 wherein said electric circuit includes an indicator lamp to indicate said irradiating unit is turned on.

20. The sterilizing apparatus claimed in claim 15 wherein said irradiating unit pivots from said closed position to said open position through an angle of about 0 to about 150 degrees.

* * * * *